(12) United States Patent
Muzslay

(10) Patent No.: US 8,292,941 B2
(45) Date of Patent: Oct. 23, 2012

(54) DELIVERY SYSTEM FOR DEPLOYMENT OF A ONE-PIECE ILIAC-BRANCH DEVICE

(75) Inventor: Heath Muzslay, Petaluma, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 853 days.

(21) Appl. No.: 12/428,619

(22) Filed: Apr. 23, 2009

(65) Prior Publication Data

US 2010/0274339 A1     Oct. 28, 2010

(51) Int. Cl.
A61F 2/06       (2006.01)
A61M 29/00     (2006.01)
A61M 31/00     (2006.01)

(52) U.S. Cl. .................. 623/1.11; 606/194; 604/508

(58) Field of Classification Search ............ 623/1.11, 623/1.12, 1.35; 606/191, 194; 604/508, 604/509
See application file for complete search history.

(56) References Cited

U.S. PATENT DOCUMENTS

| | | |
|---|---|---|
| 4,994,071 A | 2/1991 | MacGregor |
| 5,669,924 A | 9/1997 | Shaknovich |
| 5,718,724 A | 2/1998 | Goicoechea et al. |
| 5,720,735 A | 2/1998 | Dorros |
| 5,723,004 A | 3/1998 | Dereume et al. |
| 5,749,825 A | 5/1998 | Fischell et al. |
| 5,755,770 A | 5/1998 | Ravenscroft |
| 6,071,285 A | 6/2000 | Lashinski et al. |
| 6,129,738 A | 10/2000 | Lashinski et al. |
| 6,183,509 B1 | 2/2001 | Dibie |
| 6,190,349 B1 * | 2/2001 | Ash et al. .............. 604/43 |
| 6,602,225 B2 * | 8/2003 | Eidenschink et al. ... 604/101.01 |
| 6,695,832 B2 * | 2/2004 | Schon et al. .................. 604/544 |
| 7,981,093 B2 * | 7/2011 | Schon et al. .................. 604/284 |
| 8,029,457 B2 * | 10/2011 | Ash et al. ........................ 604/43 |

(Continued)

FOREIGN PATENT DOCUMENTS

EP     0804907     5/1997

(Continued)

OTHER PUBLICATIONS

Int'l Search Report for Int'l App. No. PCTUS2010/029496, Jan. 26, 2011.

*Primary Examiner* — Gary Jackson
*Assistant Examiner* — Michael Mendoza

(57) ABSTRACT

A delivery device for a bifurcated stent-graft includes a first catheter portion with a first tip and a second catheter portion with a second tip. The first and second tips each include a generally curved and tapered outer surface and complementary surfaces that face each other. The first and second tips together form a generally continuous substantially smooth shaped outer surface, for example a bullet-shaped combined tip. An outer sleeve is disposed around the first catheter portion and the second catheter portion such that at least a portion of the first tip and a portion of the second tip extend distally beyond a distal end of the outer sleeve. An inner sleeve maintains the stent-graft in a compressed configuration during delivery to the target site. The delivery device is tracked over two guidewires to the target location with the tips acting as a unit. The outer sleeve is retracted to release the first catheter portion from the second catheter portion, and the tips are tracked over a respective one of the guidewires into its respective branch vessel. The inner sleeve is retracted to deploy the stent-graft from its compressed configuration to its expanded configuration.

13 Claims, 5 Drawing Sheets

U.S. PATENT DOCUMENTS

| | | | |
|---|---|---|---|
| 8,206,354 B2 * | 6/2012 | Schon et al. | 604/164.01 |
| 2002/0077692 A1 | 6/2002 | Besselink | |
| 2003/0093109 A1 | 5/2003 | Mauch | |
| 2004/0098114 A1 | 5/2004 | Wilson et al. | |
| 2006/0079859 A1 * | 4/2006 | Elkins et al. | 604/508 |
| 2007/0191767 A1 * | 8/2007 | Hennessy et al. | 604/103.04 |
| 2007/0299499 A1 | 12/2007 | Hartley | |

FOREIGN PATENT DOCUMENTS

| | | |
|---|---|---|
| WO | WO01/41677 | 6/2001 |
| WO | WO2005/025458 | 3/2005 |
| WO | WO2005/094728 | 10/2005 |

* cited by examiner

US 8,292,941 B2

DELIVERY SYSTEM FOR DEPLOYMENT OF A ONE-PIECE ILIAC-BRANCH DEVICE

FIELD OF THE INVENTION

This invention relates generally to endovascular prostheses and, more particularly, to a delivery device and method for delivering a bifurcated endovascular prosthesis.

BACKGROUND OF THE INVENTION

Delivery devices and methods for repair of aneurysms at bifurcated vessels generally involve piecing together multiple sections of an endovascular prosthesis or stent-graft in vivo. Such devices and methods require complicated manipulations and precise delivery to specific target locations to create a bifurcated stent-graft. Certain bifurcated vessels are not conducive to deploying multiple pieces of a stent-graft in vivo. For example, repair of aneurysms at the hypogastric artery pose technical challenges because of their location deep in the pelvis.

One piece bifurcated stents are known. However, delivery systems for such bifurcated stents may simply include two combined catheter systems. Such delivery systems may be cumbersome and may be difficult to track to the target location. In particular, tips of such systems may cause damage to vessels as they are tracked through the vasculature.

Accordingly, there is a need for a delivery device and method for delivering a one-piece bifurcated stent-graft to a target location at a bifurcated vessel.

BRIEF SUMMARY OF THE INVENTION

An embodiment of a delivery device for delivering and deploying a one-piece bifurcated endoprosthesis or stent-graft includes a first catheter portion with a first tip and a second catheter portion with a second tip. The first and second tips each include a generally curved and tapered outer surface and complementarily shaped mating (complementary) surfaces that face each other. The complementary surfaces may each be flat or one may be convex and the other concave, for example. The first and second tips together form a generally bullet-shaped combined tip. An outer sleeve is disposed around the first catheter portion and the second catheter portion such that at least a portion of the first tip and a portion of the second tip extend distally beyond a distal end of the outer sleeve. An inner sleeve maintains the stent-graft in a compressed configuration during delivery to the target site.

In an embodiment of a method for delivering the one-piece bifurcated stent-graft to a target location, first and second guidewires are tracked through the vasculature to the bifurcation, with the first guidewire tracked into a first branch vessel and the second guidewire tracked into a second branch vessel. The delivery device is then tracked over the guidewires, with the first tip tracked over the first guidewire and the second tip tracked over the second guidewire. The outer sleeve keeps the first and second tips together such that they act as a unit when tracked over the first and second guidewires. When the delivery device reached the target location, the outer sleeve is retracted to release the first and second tips from each other. The delivery device is then tracked over the guidewires such that the first tip tracks over the first guidewire into the first branch vessel and the second tip tracks over the second guidewire into the second branch vessel. When the bifurcated stent-graft is in place such that a main portion of the stent-graft is in the main vessel, a first leg of the stent-graft is in the first branch vessel, and a second leg of the stent-graft is in the second branch vessel, the inner sleeve is retracted or removed to deploy the stent-graft such that it radially expands from its compressed configuration to an expanded configuration.

BRIEF DESCRIPTION OF DRAWINGS

The foregoing and other features and advantages of embodiments according to the invention will be apparent from the following description as illustrated in the accompanying drawings. The accompanying drawings, which are incorporated herein and form a part of the specification, further serve to explain the principles of the embodiments and to enable a person skilled in the pertinent art to make and use the embodiments thereof. The drawings are not to scale.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. For the stent-graft device "proximal" is the portion nearer the heart by way of blood flow path while "distal" is the portion of the stent graft further from the heart by way of blood flow path.

Figure 1:
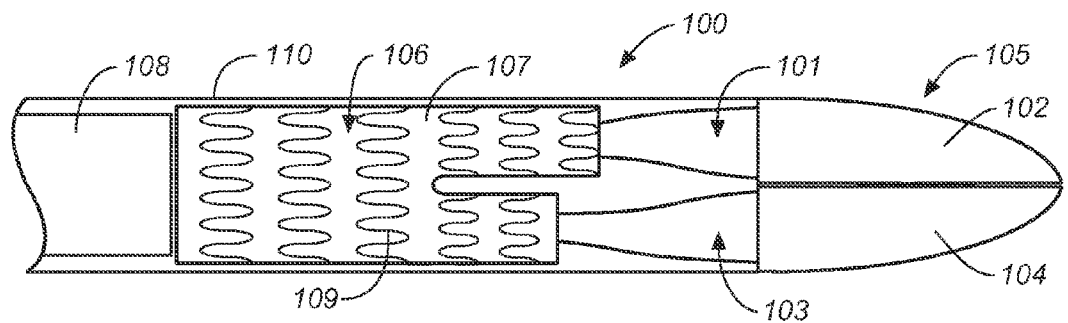
FIG. 1 is a schematic side view of a delivery device according to an embodiment hereof.

An illustrative embodiment of a distal portion of a delivery device 100 constructed in accordance with an embodiment hereof is shown in FIG. 1. Delivery device 100 is for delivering a one-piece bifurcated endoluminal prosthesis or stent-graft 106. Stent-graft 106 includes a main body, a first branch, and a second branch. Stent-graft 106 may be any suitable stent-graft. In the embodiment shown, stent-graft includes a graft material 107, such as Dacron material, and stents 109 coupled to graft material 107. Stents 109 may be made from any suitable stent material, such as stainless steel, nitinol, and cobalt-chromium alloys. Delivery device 100 includes a first distal catheter portion 101 and a second distal catheter portion 103. First distal catheter portion 101 includes a first tip 102 and second distal catheter portion 103 includes a second tip 104. Delivery device 100 further includes a stent-stop or pusher 108 and an outer sleeve 110, as shown in FIG. 1.

Delivery device 100 further includes common delivery device elements not shown, such as a proximal handle having access ports to lumens.

First and second tips 102, 104 extend distally beyond outer sleeve 110 and together form a bullet-shaped tip 105. Outer sleeve 110 holds first and second tips 102, 104 together during delivery to a target location within the vasculature, as described in more detail below. The shape of first and second tips 102, 104, (together forming a substantially smooth surface (without sharp edges or similar discontinuities) the bullet-shaped tip 105) reduces the risk of trauma to vessels during delivery to the target location. Although the combined outer shape of first and second tips 102, 104 is described as generally bullet-shaped, various atraumatic (non-traumatic) shapes could be used as known to those skilled in the art. However, it is the combined shape of tips 102, 104 that creates such a shape.

Figure 1A:
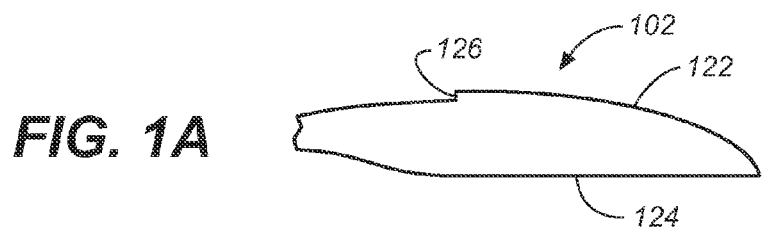
FIG. 1A is a schematic side view of a tip of the delivery device of FIG. 1.
Figure 2:
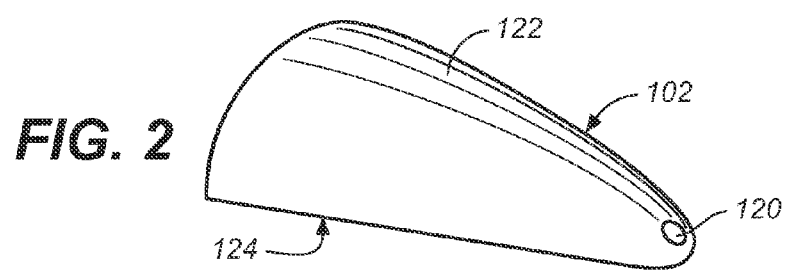
FIG. 2 is a schematic illustration of a tip for the delivery device of FIG. 1.
Figure 3:
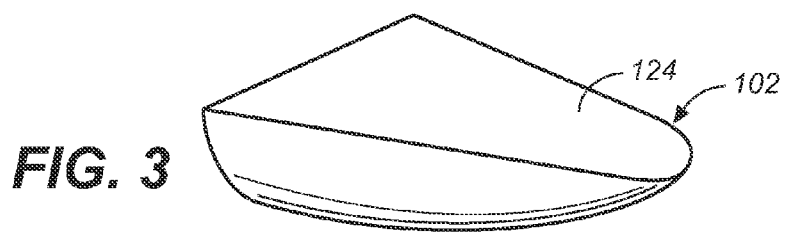
FIG. 3 is a schematic illustration of the underside of the tip of FIG. 2.

FIGS. 2 and 3 are schematic illustrations of first tip 102. First tip includes a curved and tapered outer surface 122 and a generally flat surface 124. A lumen 120 is disposed through first tip 102 and is generally used as a guidewire lumen. Second tip 104 is shaped generally the same as first tip 102 and includes a guidewire lumen disposed therethrough. In use, first and second tips 102, 104 are oriented opposite each other such that flat surface 124 of first tip 102 faces the flat surface of second tip 104, as shown in FIG. 1. As shown in FIG. 1A, tip 102 (and tip 104) may further include a lip or shoulder 126 at a proximal end thereof such that a distal end of outer sleeve 110 is not exposed to the vessel during delivery.

Figure 4:
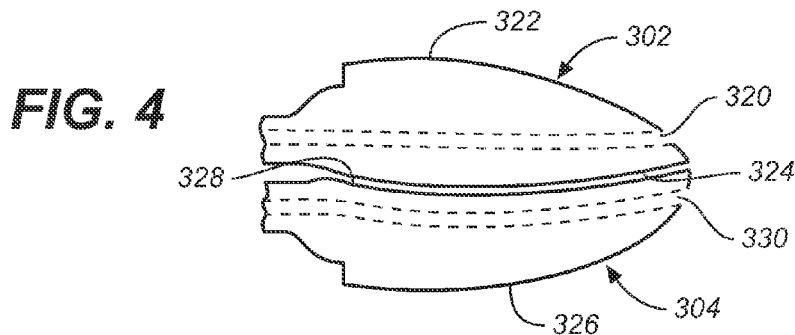
FIG. 4 is a schematic illustration of another embodiment of tips that can be used as part of the delivery device of FIG. 1.

FIG. 4 shows an alternative embodiment of a first tip 302 and a second tip 304 that can be used as part of the delivery device. The embodiment of FIG. 4 is generally the same as the embodiment of FIGS. 1-3 except that the surfaces of the tips that face each other are not generally flat. First tip 302 includes a first lumen 320, a generally convex surface 324, and a curved and tapered outer surface 322. Similarly, second tip 304 includes a second lumen 330, a generally concave surface 328, and a curved and tapered outer surface 326. Convex surface 324 of first tip 302 faces concave surface 328 of second tip 304 such that the combined outside shape of tips 302, 304 is generally bullet-shaped. The surfaces 324, 328 of tips 302, 304 that face each other are generally complementary in shape and nest with each other to form a continuous outer surface for the tip.

Figure 5:
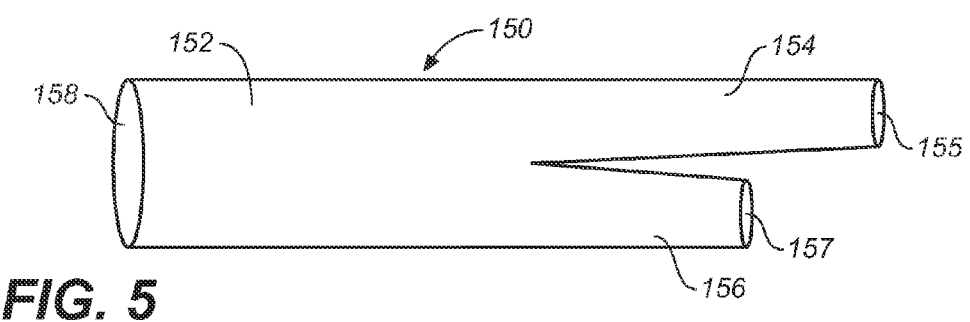
FIG. 5 is a schematic illustration of an inner sleeve of the delivery device of FIG. 1.
Figure 6:
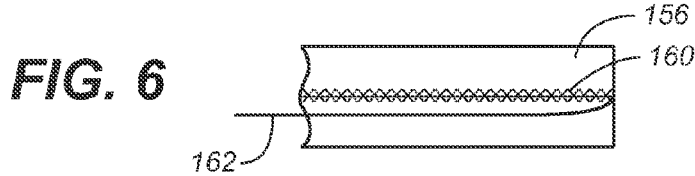
FIG. 6 is a schematic top view of a portion of the inner sleeve of FIG. 5.
Figure 7:
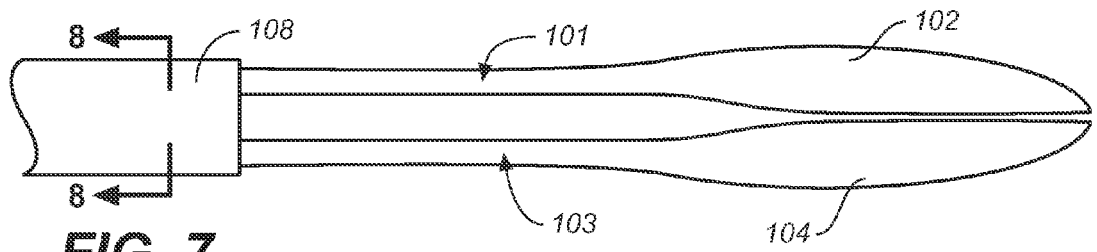
FIG. 7 is a schematic illustration of a portion of the delivery device of FIG. 1.
Figure 8:
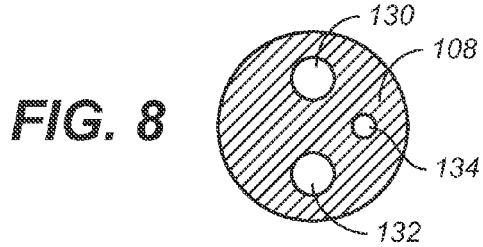
FIG. 8 is a cross-section taken along line 8-8 of FIG. 7.

Delivery device 100 further includes an inner sleeve 150 (not shown in FIG. 1). Inner sleeve 150 is shown in FIGS. 5 and 6 and in use is disposed over stent-graft 106 and within outer sleeve 110. Inner sleeve 150 includes a main body portion 152, a first branch portion 154 and a second branch portion 156. A lumen 158 is disposed through inner sleeve 150 and splits in to a first branch lumen 155 and a second branch lumen 157. FIG. 6 shows a schematic top view of second branch 156 and shows a seam 160 that can be torn or unraveled using a pull string (wire) 162. First branch 154 may include a similar seam or other means to retract or remove inner sleeve 150 from stent-graft 106. In use, inner sleeve 150 restrains self-expanding stent-graft 106 in a compressed configuration for delivery to the target location. Main body portion 152 may also include a similar seam as a separate seam or an extension of seam 160. Alternatively, main body portion 152 does not need to include a seam and after first branch 154 and second branched 156 have been released may simply be retracted using a pull wire, as known to those skilled in the art. When stent-graft 106 is at the target location, inner sleeve 150 is removed from stent-graft 106 and stent-graft 106 expands to its expanded or deployed configuration, as described in more detail below. Other means to constrain and deploy stent-graft 106 may be used, such as sutures that are ruptured using a balloon or a pull string, or other means known to those skilled in the art FIG. 7 is a schematic side view of a distal portion of pusher 108, first distal catheter portion 101, and second distal catheter portion 103. FIG. 8 is a cross-section taken along line 8-8 of FIG. 7. Pusher 108 acts to prevent stent-graft 106 from moving proximally as outer sleeve 110 and inner sleeve 150 are retracted or otherwise removed, as explained in more detail below. In the embodiment shown herein, Pusher 108 includes a first lumen 130, a second lumen 132, and a third lumen 134. First distal catheter portion 101 may extend through first lumen 130 or may be coupled to pusher 108 in alignment with first lumen 130 such that a guidewire can extend from a proximal portion of delivery device 100 through first distal catheter portion 101 and out of lumen 120 of tip 102. Similarly, second distal catheter portion 103 may extend through second lumen 130 or may be coupled to pusher 108 in alignment with second lumen 130 such that a guidewire can extend from a proximal portion of delivery device 100 through second distal catheter portion 103 and out of the lumen of tip 104. Third lumen 134 of pusher 108 may includes pull wire 162 disposed therethrough and/or other pull wires for inner sleeve 150. Third lumen 134 may be omitted and pull wire 162 may extend between pusher 108 and outer sleeve 110, for example.

Figure 9:
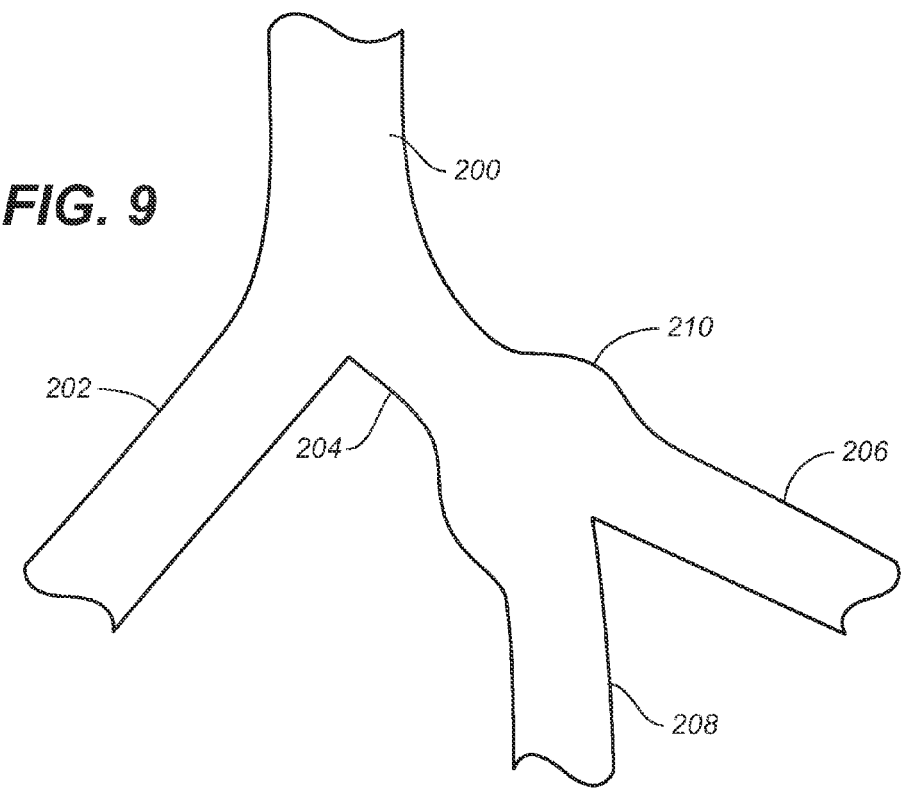
FIGS. 9-14 are schematic illustrations of progressive steps of a method for delivering and deploying a one-piece bifurcated stent-graft to a target location using the delivery device of FIG. 1.

FIGS. 9-14 schematically show progressive steps of a method of delivering and deploying stent-graft 106 to a target site at a bifurcated vessel. In particular, FIGS. 9-14 show a method of delivering and deploying stent-graft 106 to the location where the left common iliac artery 204 branches into the left external iliac artery 206 and the hypogastric or internal iliac artery 208. The left common iliac artery 204 branches with the right common iliac artery 202 from the abdominal aorta 200. As shown in FIG. 9 an aneurysm 210 in the left common iliac artery 204 near the bifurcation into the left external iliac artery 206 and the hypogastric artery 208 may be treated with a stent-graft such as stent-graft 106. Although delivery device 100 is described with respect to the target location in the left common iliac artery 204, it would be understood by those skilled in the art that such a delivery device may be useful in other locations to deliver bifurcated stent-grafts.

Figure 10:
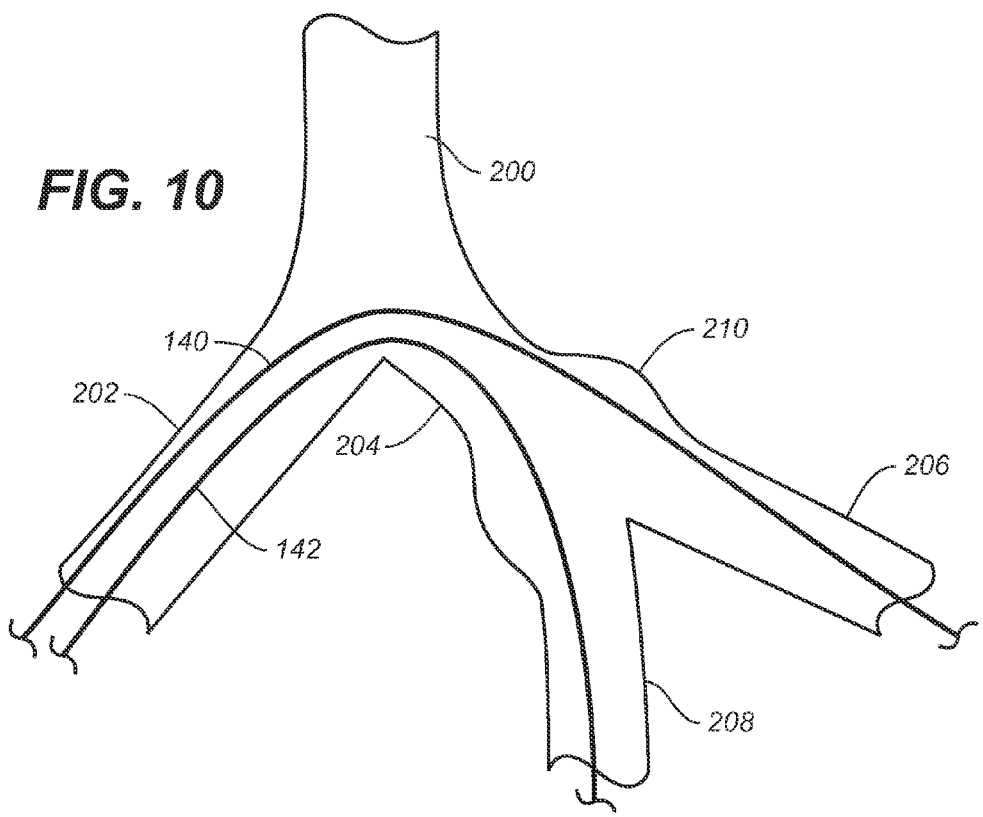

FIG. 10 shows a first guidewire 140 and a second guidewire 142 advanced through the right common iliac artery 202 and into the left common iliac artery 204. First guidewire 140 is advanced into the left external iliac artery 206 and second guidewire 142 is advanced into the hypogastric artery 208. Guidewires 140, 142 are typically inserted into the femoral artery as known to those skilled in the art.

Figure 11:
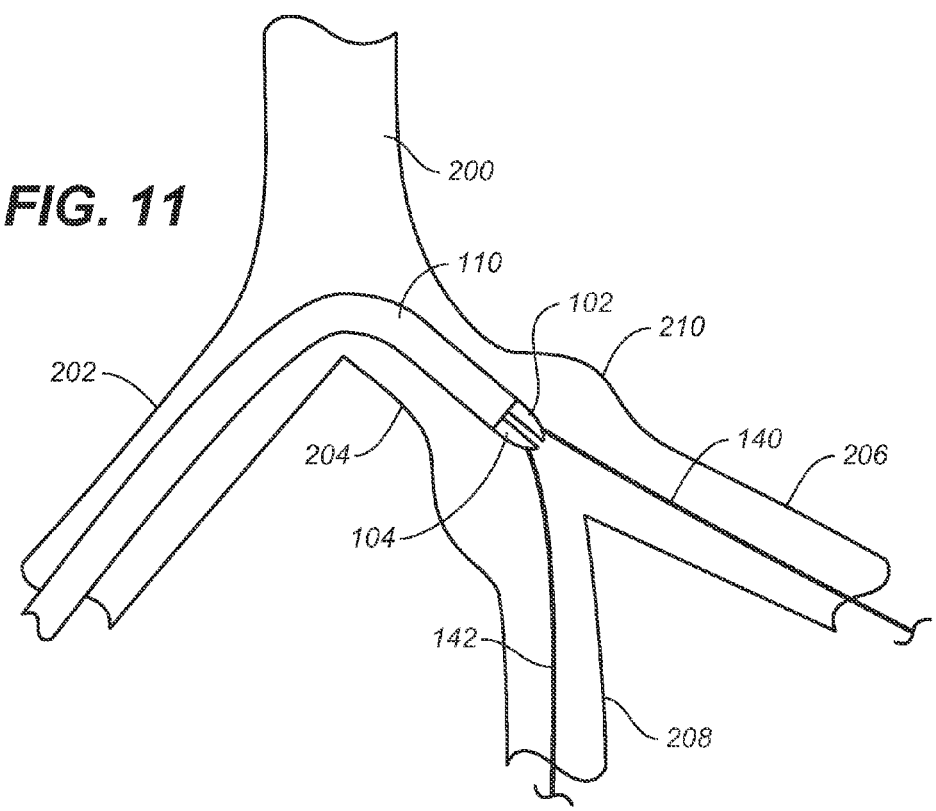

FIG. 11 shows delivery device 100 advanced over first and second guidewires 140, 142. In particular, first guidewire 140 may be back-loaded into lumen 120 of first tip 102 and second guidewire 142 may be back-loaded into the lumen of second tip 104. First and second tips 102, 104 are held together by outer sleeve 110 such that first and second tips 102, 104 and first distal catheter portion 101 and second distal catheter portion 103 are advanced over guidewires 140, 142 as a unit. Delivery device 100 is advanced into the left common iliac artery 204 to a location proximal to the bifurcation. Stent-graft 106 is disposed within outer sleeve 110 and inner sleeve 150 in its compressed or delivery configuration.

Figure 12:
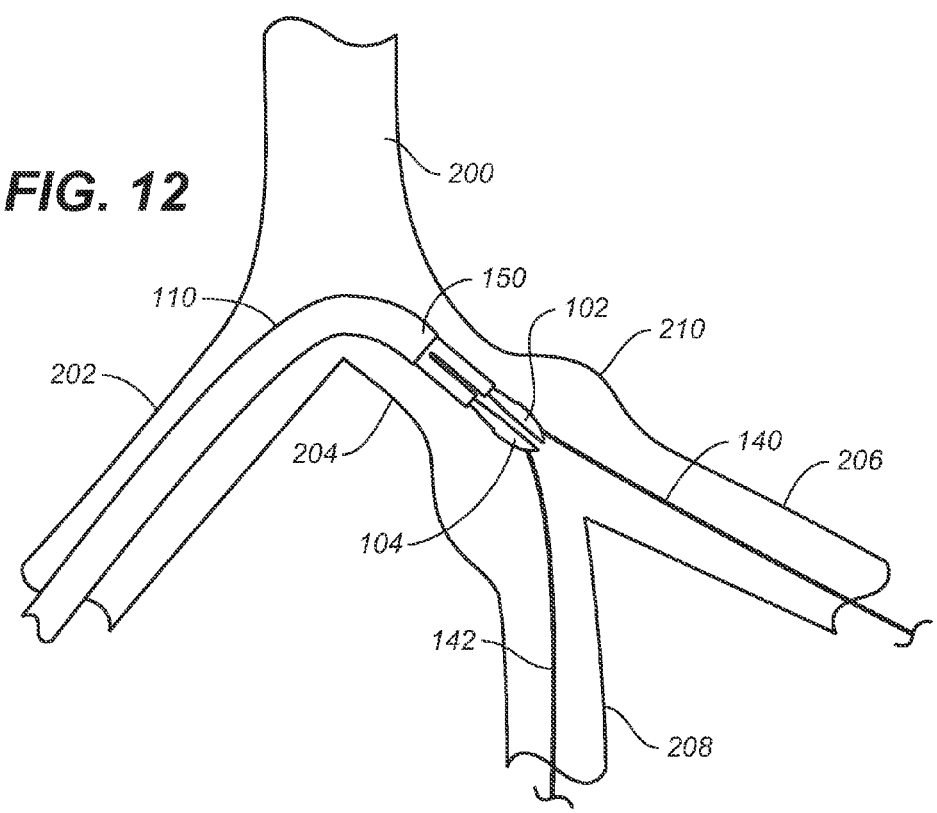
Figure 13:
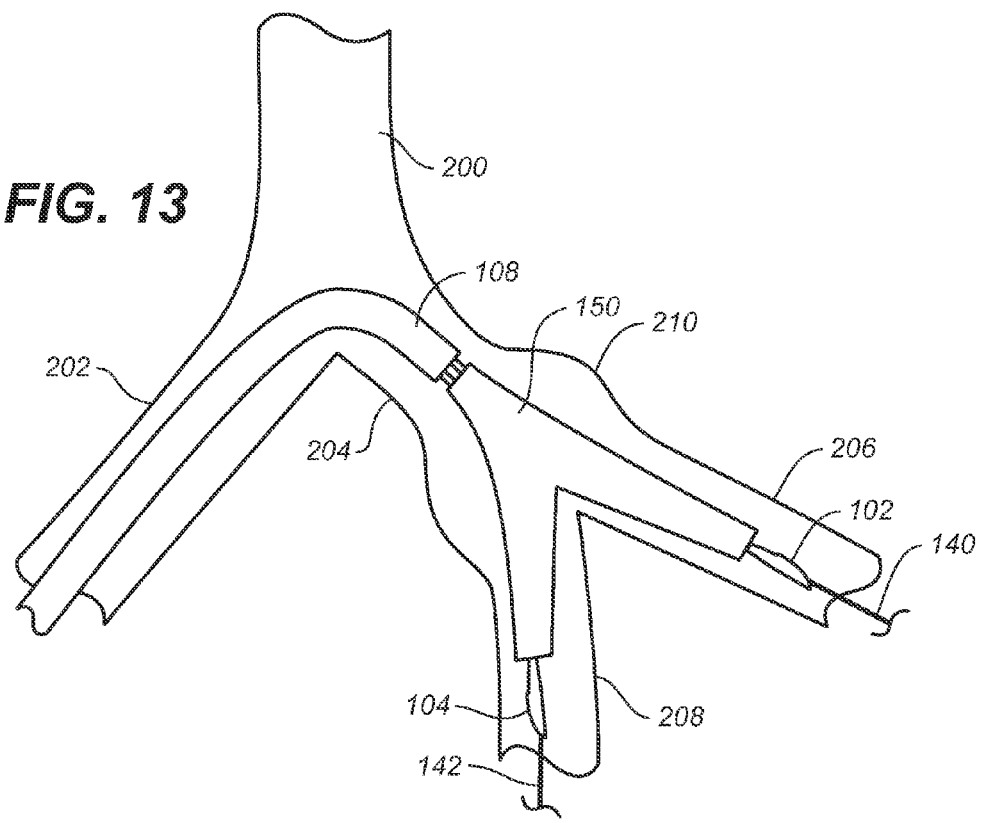

FIG. 12 shows outer sleeve 110 retracted proximally. Retracting outer sleeve 110 frees first distal catheter portions 101 from second distal catheter portion 103 and first tip 102 from second tip 104. Once tips 102, 104 are freed from each other, delivery device 100 can be advanced distally over guidewires 140, 142. Because tips 102, 104 are separated, first tip 102 follows along first guidewire 140 into left external iliac artery 206 and second tip 104 follows along second guidewire 142 into hypogastric artery 208, as shown in FIG. 13.

Figure 14:
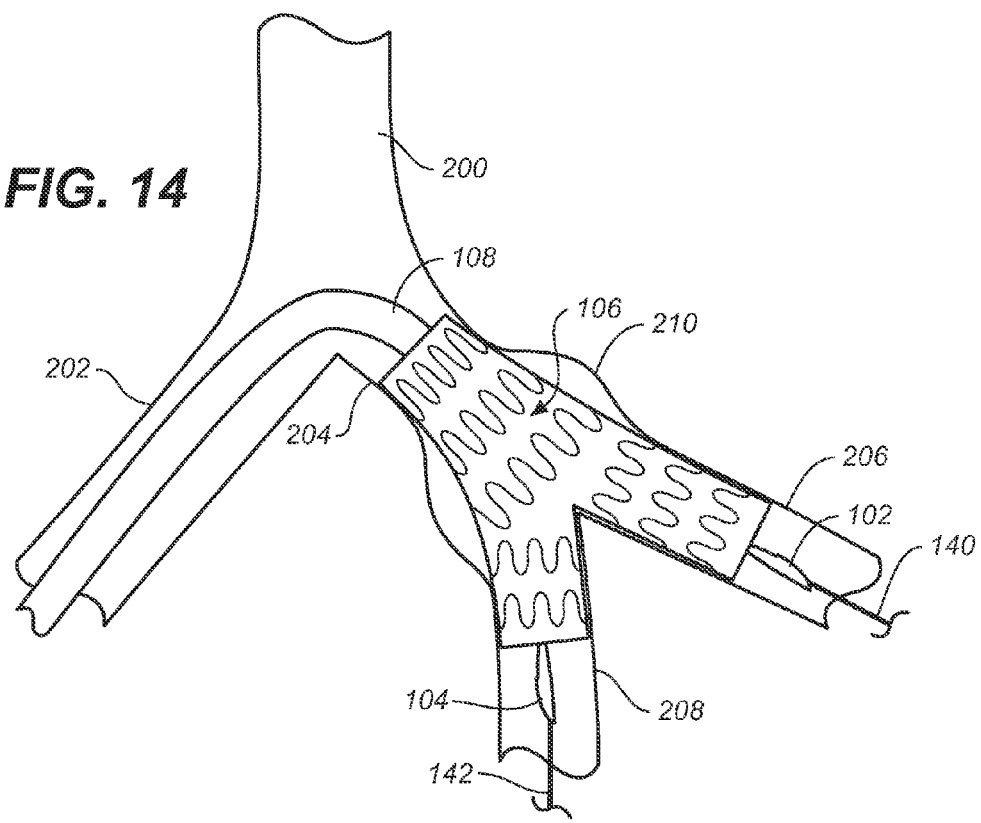

Once in position, inner sleeve 150 may be retracted or otherwise removed. Stent-graft 106 radially expands from its compressed configuration to its expanded or deployed configuration, as shown in FIG. 14. Stent-graft 106 is in place to exclude aneurysm 210 and provide blood flow to left external iliac artery 206 and hypogastric artery 208.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. It will also be understood that each feature of each embodiment discussed herein, and of each reference cited herein, can be used in combination with the features of any other embodiment. All patents and publications discussed herein are incorporated by reference herein in their entirety.

What is claimed is:

1. A delivery device for a one-piece bifurcated endovascular graft comprising:
    a first catheter portion including a first tip at a distal end of the first catheter portion, the first tip including a first lumen disposed therethrough, a first surface and a second generally curved tapered surface opposite the first surface;
    a second catheter portion including a second tip at a distal end of the second catheter portion, the second tip including a second lumen disposed therethrough, a third surface and a fourth generally curved, tapered surface opposite the third surface; and
    an outer sleeve disposed around the first catheter portion and the second catheter portion such that at least a portion of the first tip and a portion of the second tip extend distally beyond a distal end of the outer sleeve;
    wherein the first surface and the third surface have complementary shapes such that first tip and the second tip together form a combined continuous substantially smooth surface tip.

2. The delivery device of claim 1, wherein the combined tip forms a generally bullet shaped combined tip.

3. The delivery device of claim 2, wherein the first surface and the second surface are generally flat.

4. The delivery device of claim 2, wherein the first surface is generally concave and the second surface is generally convex.

5. The delivery device of claim 2, further comprising an inner sleeve disposed within a lumen of the outer sleeve, wherein the endovascular graft is disposed within the inner sleeve.

6. The delivery device of claim 5, wherein the inner sleeve includes a main vessel portion, a first branch portion extending from the main vessel portion, and a second branch portion extending from the main vessel portion.

7. The delivery device of claim 5, further comprising a pusher disposed within the lumen of the outer sleeve and proximal to the endovascular graft.

8. The delivery device of claim 2, wherein the second generally curved, tapered surface includes a first shoulder at a proximal end thereof, and wherein the fourth generally curved, tapered surface includes a second shoulder at a proximal end thereof, and wherein the distal end of the outer sleeve abuts the first shoulder and the second shoulder.

9. A method for delivering a one-piece bifurcated graft having a main portion, a first leg, and a second leg to a target location at a bifurcated vessel having a main vessel, a first branch vessel, and a second branch vessel, comprising the steps of;
    advancing a first guidewire through the main vessel and into the first branch vessel;
    advancing a second guidewire through the main vessel and into the second branch vessel;
    advancing a delivery device over the first guidewire and the second guidewire to the target location, wherein the delivery device includes a first catheter portion including a first tip, a second catheter portion including a second tip, and an outer sleeve disposed around the first and second catheter portions such that the first and second catheter portions can be advanced together, wherein at least a portion of the first tip and at least a portion of the second tip extend distally beyond a distal end of the outer sleeve, wherein the first tip and the second tip combined form a generally bullet shape, and wherein the graft is disposed within the delivery device in a compressed configuration;
    retracting the outer sleeve proximally such that the first catheter portion and the second catheter portion may move independent of each other;
    further advancing the delivery device such that the first tip advances over the first guidewire into the first branch vessel such that the first leg of the graft is disposed within the first branch vessel and the second tip advances over the second guidewire into the second branch vessel such that the second leg of the graft is disposed within the second branch vessel; and
    deploying the graft such that the graft radially expands from the compressed configuration to an expanded configuration.

10. The method of claim 9, wherein the main vessel is the left common iliac artery, the first branch vessel is the left external iliac artery, and the second branch vessel is the hypogastric artery.

11. The method of claim 9, wherein the first tip includes a first surface and a second generally curved, tapered surface opposite the first surface, wherein the second tip includes a third surface and a fourth generally curved, tapered surface opposite the third surface, and wherein the first surface and the third surface have complementary shapes such that first tip and the second together form the combined generally bullet-shaped tip.

12. The method of claim 11, wherein the first surface and the third surface are generally flat.

13. The method of claim 11, wherein the first surface is generally concave and the third surface is generally convex.

* * * * *